United States Patent
Ochs et al.

(10) Patent No.: US 9,179,876 B2
(45) Date of Patent: Nov. 10, 2015

(54) SYSTEMS AND METHODS FOR IDENTIFYING PORTIONS OF A PHYSIOLOGICAL SIGNAL USABLE FOR DETERMINING PHYSIOLOGICAL INFORMATION

(75) Inventors: James Ochs, Seattle, WA (US); Scott McGonigle, Edinburgh (GB); Paul Addison, Midlothian (GB); James Watson, Fife (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 555 days.

(21) Appl. No.: 13/459,855

(22) Filed: Apr. 30, 2012

(65) Prior Publication Data
US 2013/0289413 A1   Oct. 31, 2013

(51) Int. Cl.
A61B 6/00 (2006.01)
A61B 5/00 (2006.01)
A61B 5/08 (2006.01)
A61B 5/1455 (2006.01)
A61B 5/0205 (2006.01)

(52) U.S. Cl.
CPC .......... *A61B 5/7203* (2013.01); *A61B 5/0816* (2013.01); *A61B 5/14551* (2013.01); *A61B 5/7278* (2013.01); *A61B 5/743* (2013.01); *A61B 5/0205* (2013.01); *A61B 5/7246* (2013.01)

(58) Field of Classification Search
CPC ......................................................... A61B 6/01
USPC ......................................... 600/532, 476, 323
See application file for complete search history.

(56) References Cited

U.S. PATENT DOCUMENTS

| | | |
|---|---|---|
| 5,188,108 A | 2/1993 | Secker |
| 5,285,783 A | 2/1994 | Secker |
| 5,285,784 A | 2/1994 | Secker |
| 5,368,026 A | 11/1994 | Swedlow et al. |
| 5,398,682 A | 3/1995 | Lynn |
| 5,558,096 A | 9/1996 | Palatnik |
| 5,584,295 A | 12/1996 | Muller et al. |
| 5,588,425 A | 12/1996 | Sackner et al. |
| 5,605,151 A | 2/1997 | Lynn |
| 5,862,805 A | 1/1999 | Nitzan |
| 5,865,736 A | 2/1999 | Baker et al. |

(Continued)

FOREIGN PATENT DOCUMENTS

CN   202067273   12/2011
EP   0072601 A1   2/1983

(Continued)

OTHER PUBLICATIONS

International Search Report and Written Opinion of the International Searching Authority for application No. PCT/US2013/037700, mailed on Sep. 12, 2013.

(Continued)

*Primary Examiner* — Joel F Brutus
(74) *Attorney, Agent, or Firm* — Shvarts & Leiz LLP

(57) ABSTRACT

A patient monitoring system may determine portions of a PPG signal that correspond to artifacts, to a baseline shift that exceeds a threshold, or to a pulse-to-pulse variability that exceeds a threshold. The patient monitoring system may identify a contiguous portion of the PPG signal that does not include the determined portions. The contiguous portion of the PPG signal may be used to determine physiological information.

20 Claims, 9 Drawing Sheets

(56) References Cited

U.S. PATENT DOCUMENTS

| | | | |
|---|---|---|---|
| 5,891,023 A | 4/1999 | Lynn | |
| 6,002,952 A | 12/1999 | Diab et al. | |
| 6,035,223 A | 3/2000 | Baker | |
| 6,081,742 A | 6/2000 | Amano et al. | |
| 6,095,984 A | 8/2000 | Amano et al. | |
| 6,129,675 A | 10/2000 | Jay | |
| 6,135,966 A | 10/2000 | Ko | |
| 6,178,261 B1 | 1/2001 | Williams et al. | |
| 6,223,064 B1 | 4/2001 | Lynn | |
| 6,229,856 B1 | 5/2001 | Diab et al. | |
| 6,238,351 B1 | 5/2001 | Orr et al. | |
| 6,325,761 B1 | 12/2001 | Jay | |
| 6,334,065 B1 | 12/2001 | Al-Ali et al. | |
| 6,342,039 B1 | 1/2002 | Lynn et al. | |
| 6,350,242 B1 | 2/2002 | Doten et al. | |
| 6,405,076 B1 | 6/2002 | Taylor et al. | |
| 6,463,311 B1 | 10/2002 | Diab | |
| 6,506,153 B1 | 1/2003 | Littek et al. | |
| 6,561,986 B2 | 5/2003 | Baura et al. | |
| 6,564,077 B2 | 5/2003 | Mortara | |
| 6,606,511 B1 | 8/2003 | Ali et al. | |
| 6,609,016 B1 | 8/2003 | Lynn | |
| 6,684,090 B2 | 1/2004 | Ali et al. | |
| 6,694,178 B1 | 2/2004 | Soula et al. | |
| 6,702,752 B2 | 3/2004 | Dekker | |
| 6,709,402 B2 | 3/2004 | Dekker | |
| 6,748,252 B2 | 6/2004 | Lynn et al. | |
| 6,754,516 B2 | 6/2004 | Mannheimer | |
| 6,760,608 B2 | 7/2004 | Lynn | |
| 6,783,498 B2 | 8/2004 | Sackner et al. | |
| 6,816,741 B2 | 11/2004 | Diab | |
| 6,839,581 B1 | 1/2005 | El-Solh et al. | |
| 6,896,661 B2 | 5/2005 | Dekker | |
| 6,905,470 B2 | 6/2005 | Lee et al. | |
| 6,925,324 B2 | 8/2005 | Shusterman | |
| 6,931,269 B2 | 8/2005 | Terry | |
| 6,966,878 B2 | 11/2005 | Schoisswohl et al. | |
| 6,970,792 B1 | 11/2005 | Diab | |
| 6,980,679 B2 | 12/2005 | Jeung et al. | |
| 7,020,507 B2 | 3/2006 | Scharf et al. | |
| 7,035,679 B2 | 4/2006 | Addison et al. | |
| 7,043,293 B1 | 5/2006 | Baura | |
| 7,044,918 B2 | 5/2006 | Diab | |
| 7,070,566 B2 | 7/2006 | Medero et al. | |
| 7,079,888 B2 | 7/2006 | Oung et al. | |
| 7,147,601 B2 | 12/2006 | Marks et al. | |
| 7,177,682 B2 | 2/2007 | Lovett | |
| 7,190,261 B2 | 3/2007 | Al-Ali | |
| 7,215,986 B2 | 5/2007 | Diab et al. | |
| 7,218,966 B2 | 5/2007 | Haefner | |
| 7,254,425 B2 | 8/2007 | Lowery et al. | |
| 7,283,870 B2 | 10/2007 | Kaiser et al. | |
| 7,336,982 B2 | 2/2008 | Yoo | |
| 7,355,512 B1 | 4/2008 | Al-Ali | |
| 7,367,339 B2 | 5/2008 | Bickle | |
| 7,367,949 B2 | 5/2008 | Korhonen et al. | |
| 7,398,115 B2 | 7/2008 | Lynn | |
| 7,403,806 B2 | 7/2008 | Norris | |
| 7,407,486 B2 | 8/2008 | Huiku et al. | |
| 7,415,297 B2 | 8/2008 | Al-Ali et al. | |
| 7,438,683 B2 | 10/2008 | Al-Ali et al. | |
| 7,440,787 B2 | 10/2008 | Diab | |
| 7,470,235 B2 | 12/2008 | Moriya et al. | |
| 7,485,095 B2 | 2/2009 | Shusterman | |
| 7,496,393 B2 | 2/2009 | Diab et al. | |
| 7,499,835 B2 | 3/2009 | Weber et al. | |
| 7,523,011 B2 | 4/2009 | Akiyama et al. | |
| 7,561,912 B2 | 7/2009 | Schatz et al. | |
| 7,610,324 B2 | 10/2009 | Troyansky et al. | |
| 7,690,378 B1 | 4/2010 | Turcott | |
| 7,801,591 B1 | 9/2010 | Shusterman | |
| 7,869,980 B2 | 1/2011 | Casler et al. | |
| 7,894,868 B2 | 2/2011 | Al-Ali et al. | |
| 7,899,507 B2 | 3/2011 | Al-Ali et al. | |
| 7,976,472 B2 | 7/2011 | Kiani | |
| 7,988,637 B2 | 8/2011 | Diab | |
| 8,019,400 B2 | 9/2011 | Diab et al. | |
| 8,046,040 B2 | 10/2011 | Al-Ali et al. | |
| 8,130,105 B2 | 3/2012 | Al-Ali et al. | |
| 8,203,438 B2 | 6/2012 | Kiani et al. | |
| 8,275,553 B2 | 9/2012 | Ochs et al. | |
| 8,364,225 B2 | 1/2013 | Addison et al. | |
| 2002/0117173 A1 | 8/2002 | Lynn et al. | |
| 2003/0036685 A1 | 2/2003 | Goodman | |
| 2003/0158466 A1 | 8/2003 | Lynn | |
| 2003/0163054 A1 | 8/2003 | Dekker | |
| 2004/0015091 A1 | 1/2004 | Greenwald et al. | |
| 2005/0004479 A1 | 1/2005 | Townsend et al. | |
| 2005/0022606 A1 | 2/2005 | Partin et al. | |
| 2005/0027205 A1 | 2/2005 | Tarassenko et al. | |
| 2005/0049470 A1 | 3/2005 | Terry | |
| 2005/0070774 A1 | 3/2005 | Addison et al. | |
| 2005/0222502 A1 | 10/2005 | Cooper | |
| 2005/0222503 A1 | 10/2005 | Dunlop et al. | |
| 2006/0122476 A1 | 6/2006 | Van Slyke | |
| 2006/0192667 A1 | 8/2006 | Al-Ali | |
| 2006/0211930 A1 | 9/2006 | Scharf et al. | |
| 2006/0217614 A1 | 9/2006 | Takala et al. | |
| 2006/0258921 A1 | 11/2006 | Addison et al. | |
| 2007/0004977 A1 | 1/2007 | Norris | |
| 2007/0010723 A1 | 1/2007 | Uetela et al. | |
| 2007/0032639 A1 | 2/2007 | Gottesman et al. | |
| 2007/0073120 A1 | 3/2007 | Li et al. | |
| 2007/0073124 A1 | 3/2007 | Li et al. | |
| 2007/0129636 A1 | 6/2007 | Friedman et al. | |
| 2007/0149890 A1 | 6/2007 | Li et al. | |
| 2007/0213619 A1 | 9/2007 | Linder | |
| 2007/0213621 A1 | 9/2007 | Reisfeld et al. | |
| 2007/0255146 A1 | 11/2007 | Andrews et al. | |
| 2007/0293896 A1 | 12/2007 | Haefner | |
| 2008/0077022 A1 | 3/2008 | Baker | |
| 2008/0167540 A1 | 7/2008 | Korhonen et al. | |
| 2008/0200775 A1 | 8/2008 | Lynn | |
| 2009/0247837 A1 | 10/2009 | Ochs et al. | |
| 2009/0326349 A1 | 12/2009 | McGonigle | |
| 2009/0326395 A1 | 12/2009 | Watson | |
| 2009/0326831 A1 | 12/2009 | McGonigle et al. | |
| 2010/0014725 A1* | 1/2010 | Watson et al. | 382/128 |
| 2010/0113904 A1 | 5/2010 | Batchelder et al. | |
| 2010/0113908 A1 | 5/2010 | Vargas et al. | |
| 2010/0113909 A1 | 5/2010 | Batchelder et al. | |
| 2010/0286495 A1* | 11/2010 | McGonigle et al. | 600/330 |
| 2011/0026784 A1 | 2/2011 | Van Slyke et al. | |
| 2011/0066062 A1 | 3/2011 | Banet et al. | |
| 2011/0071406 A1 | 3/2011 | Addison et al. | |

FOREIGN PATENT DOCUMENTS

| | | |
|---|---|---|
| EP | 1344488 A2 | 9/2004 |
| EP | 1507474 B1 | 2/2009 |
| WO | WO 00/21438 | 4/2000 |
| WO | WO 03/000125 A1 | 1/2003 |
| WO | WO 03/055395 A1 | 7/2003 |
| WO | WO 03/084396 A1 | 10/2003 |
| WO | WO 2004/075746 A2 | 9/2004 |
| WO | WO 2010/030238 A1 | 3/2010 |

OTHER PUBLICATIONS

Stagg and Gennser, "Electronic analysis of foetal breathing movements: A practical application of phase-locked-loop principles," Journal of Med. Eng. and Tech., Sep. 1978, vol. 2, No. 5, pp. 246-249.

Rapaport and Cousin, "New phase-lock tracking instrument for foetal breathing monitoring," Med. & Biol. Eng. & Comp. 1982, vol. 20, pp. 1-6.

Lindberg, L.G., Ughall, H., Oberg, P.A., "Monitoring of respiratory and heart rates using a fibre-optic sensor," Medical & Biological Engineering & Computing, Sep. 1992, pp. 533-537.

* cited by examiner

SYSTEMS AND METHODS FOR IDENTIFYING PORTIONS OF A PHYSIOLOGICAL SIGNAL USABLE FOR DETERMINING PHYSIOLOGICAL INFORMATION

The present disclosure relates to physiological signal processing, and more particularly relates to identifying portions of a physiological signal that are usable for determining physiological information.

SUMMARY

A method for determining physiological information from a photoplethysmograph (PPG) signal comprises processing equipment determining the presence of an artifact in a first portion of the PPG signal, determining the presence of a baseline shift that exceeds a baseline shift threshold in a second portion of the PPG signal, and determining a pulse-to-pulse variability that exceeds a variability threshold in a third portion of the PPG signal. The method includes identifying a contiguous portion of the PPG signal that does not include the first portion, the second portion, and the third portion, wherein the contiguous portion is at least a minimum length, and determining the physiological information based on the contiguous portion.

A non-transitory computer-readable storage medium for use in determining physiological information from a PPG signal has computer program instructions recorded thereon for determining the presence of an artifact in a first portion of the PPG signal, determining the presence of a baseline shift that exceeds a baseline shift threshold in a second portion of the PPG signal, and determining a pulse-to-pulse variability that exceeds a variability threshold in a third portion of the PPG signal. The computer readable storage medium includes computer program instructions for identifying a contiguous portion of the PPG signal that does not include the first portion, the second portion, and the third portion, wherein the contiguous portion is at least a minimum length, and determining the physiological information based on the contiguous portion.

A patient monitoring system comprises processing equipment configured to determine the presence of an artifact in a first portion of the PPG signal, determine the presence of a baseline shift that exceeds a baseline shift threshold in a second portion of the PPG signal, and determine a pulse-to-pulse variability that exceeds a variability threshold in a third portion of the PPG signal. The processing equipment is configured to identify a contiguous portion of the PPG signal that does not include the first portion, the second portion, and the third portion, wherein the contiguous portion is at least a minimum length, and determine the physiological information based on the contiguous portion.

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
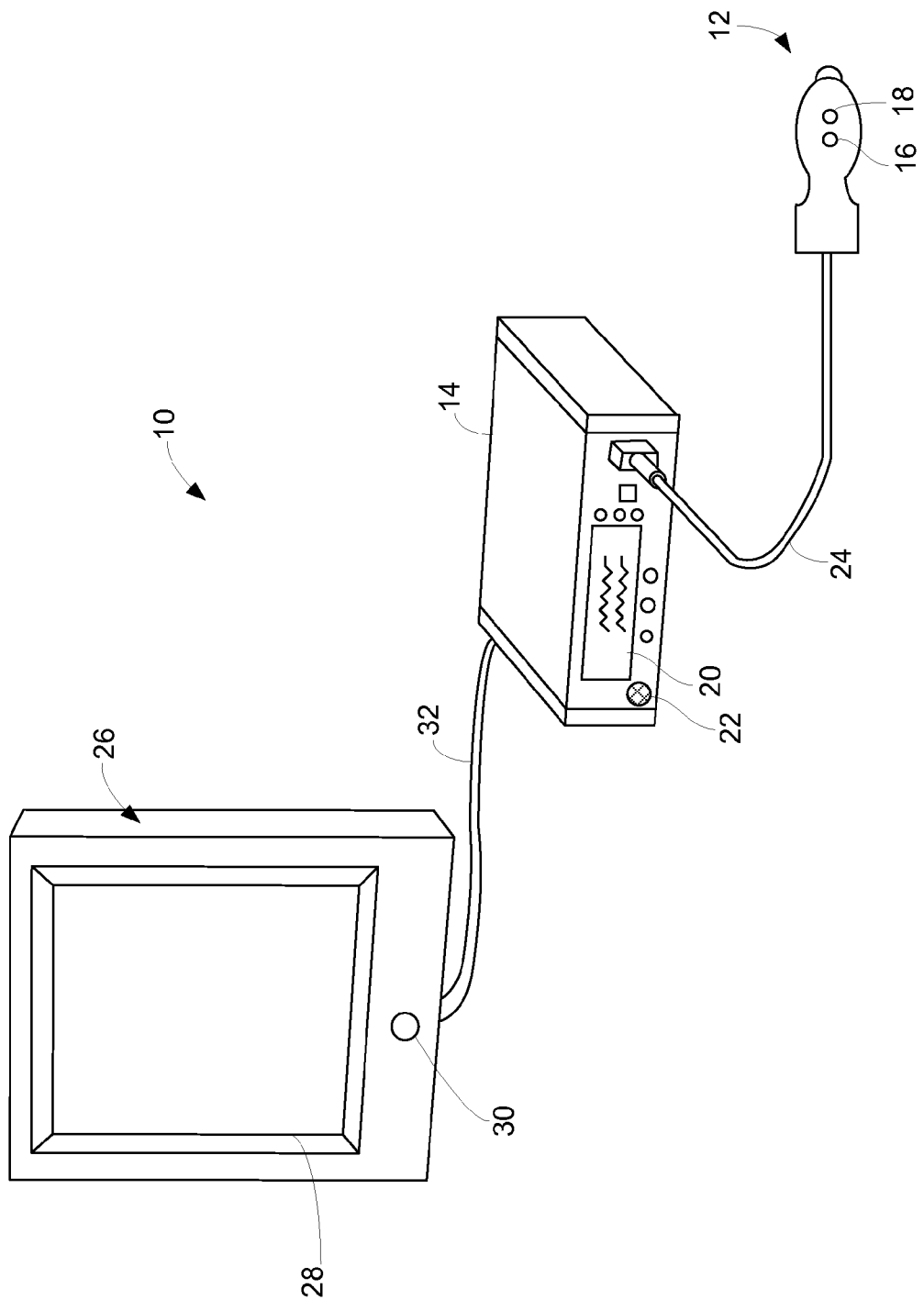
FIG. 1 shows an illustrative patient monitoring system in accordance with some embodiments of the present disclosure.

Physiological monitoring systems rely on signals that are often corrupted or contain morphologies that produce erratic or unreliable results when processing occurs to extract useful physiological information. The present disclosure describes a system that addresses these concerns by identifying portions of a physiological signal, such as a photoplethysmograph (PPG) signal, that, when processed, are likely to result in erratic or unreliable results.

A patient monitoring system may receive a physiological signal such as a PPG signal. The patient monitoring system may identify portions of the PPG signal that correspond to artifacts due to patient motion, invalid measurements, sensor errors (e.g., sensor off or disconnected), or other reasons. These portions of the signal may be identified (e.g., flagged) and may be associated with the PPG signal such that portions of the PPG signal may be identified for additional processing. The patient monitoring system may also determine $SpO_2$ and pulse rate values, and determine whether these values are out of range.

The patient monitoring system may also analyze the PPG signal to identify large baseline shifts and a large pulse-to-pulse variability. Large baseline shifts may be identified when the absolute value of the PPG baseline signal exceeds a threshold. A large pulse-to-pulse variability may be identified when the percentage difference in the pulse period of consecutive pulses exceeds a threshold. Portions of the signal corresponding to a large baseline shift and/or large pulse-to-pulse variability may be identified for further processing.

The patient monitoring system may identify the largest contiguous portion of the PPG signal that does not correspond to a large baseline shift and further identify an additional buffer region. The remaining portions of the PPG signal (including the buffer region) may be discarded, replaced, or otherwise ignored. The patient monitoring system may also identify the largest contiguous portion of the PPG signal that does not correspond to an artifact, large pulse-to-pulse variability, or out of range values. The contiguous portion may be required to be of a particular minimum length. The remaining portions of the PPG signal may be discarded, replaced, or otherwise ignored. The remaining usable portion of the PPG signal may be used to determine physiological information such as respiration information.

For purposes of clarity, the present disclosure is written in the context of the physiological signal being a PPG signal generated by a pulse oximetry system. It will be understood that any other suitable physiological signal or any other suitable system may be used in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda, t) = I_0(\lambda) \exp(-(s\beta_o(\lambda) + (1-s)\beta_r(\lambda))l(t)) \quad (1)$$

where:
$\lambda$=wavelength;
t=time;
I=intensity of light detected;
$I_0$=intensity of light transmitted;
S=oxygen saturation;
$\beta_o, \beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_0 - (s\beta_o + (1-s)\beta_r)l \quad (2)$$

2. Eq. 2 is then differentiated with respect to time to yield $$\frac{d \log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d \log I(\lambda_R)/dt}{d \log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})}. \quad (4)$$

4. Solving for S yields $$s = \frac{\frac{d \log I(\lambda_{IR})}{dt}\beta_r(\lambda_R) - \frac{d \log I(\lambda_R)}{dt}\beta_r(\lambda_{IR})}{\frac{d \log I(\lambda_R)}{dt}(\beta_o(\lambda_{IR}) - \beta_r(\lambda_{IR})) - \frac{d \log I(\lambda_{IR})}{dt}(\beta_o(\lambda_R) - \beta_r(\lambda_R))}. \quad (5)$$

5. Note that, in discrete time, the following approximation can be made:

$$\frac{d \log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d \log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d \log I(\lambda_R)}{dt}}{\frac{d \log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for S using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (11)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_{IR})}$$

$$= R,$$

which defines a cluster of points whose slope of y versus x will give R when $$x = [I(t_2, \lambda_{IR}) - I(t_1, \lambda_{IR})]I(t_1, \lambda_R) \quad (12)$$

and $$y = [I(t_2, \lambda_R) - I(t_1, \lambda_R)]I(t_1, \lambda_{IR}) \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to some embodiments, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation, and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may allow communication between monitor 14 and sensor unit 12.

Patient monitoring system 10 may also include display monitor 26. Monitor 14 may be in communication with display monitor 26. Display monitor 26 may be any electronic device that is capable of communicating with monitor 14 and calculating and/or displaying physiological parameters (e.g., a general purpose computer, tablet computer, smart phone, or an application-specific device). Display monitor 26 may include a display 28 and user interface 30. Display 28 may include touch screen functionality to allow a user to interface with display monitor 26 by touching display 28 and utilizing motions. User interface 30 may be any interface that allows a user to interact with display monitor 26 (e.g., a keyboard, one or more buttons, a camera, a microphone, or a touchpad).

Monitor 14 and display monitor 26 may communicate utilizing any suitable transmission medium, including wireless (e.g., WiFi, Bluetooth, etc.), wired (e.g., USB, Ethernet, etc.), or application-specific connections. In an exemplary embodiment, monitor 14 and display monitor 26 may be connected via cable 32. Monitor 14 and display monitor 26 may communicate utilizing standard or proprietary communications protocols, such as the Standard Host Interface Protocol (SHIP) developed and used by Covidien of Mansfield, Mass. In addition, monitor 14, display monitor 26, or both may be coupled to a network to enable the sharing of information with servers or other workstations (not shown). Monitor 14, display monitor 26, or both may be powered by a battery (not shown) or by a conventional power source such as a wall outlet.

Monitor 14 may transmit calculated physiological parameters (e.g., pulse rate, blood oxygen saturation, and respiration information) to display monitor 26. In some embodiments, monitor 14 may transmit a PPG signal, data representing a PPG signal, or both to display monitor 26, such that some or all calculated physiological parameters (e.g., pulse rate, blood oxygen saturation, and respiration information) may be calculated at display monitor 26. In an exemplary embodiment, monitor 14 may calculate pulse rate and blood oxygen saturation, while display monitor 26 may calculate respiration information such as a respiration rate.

Figure 2:
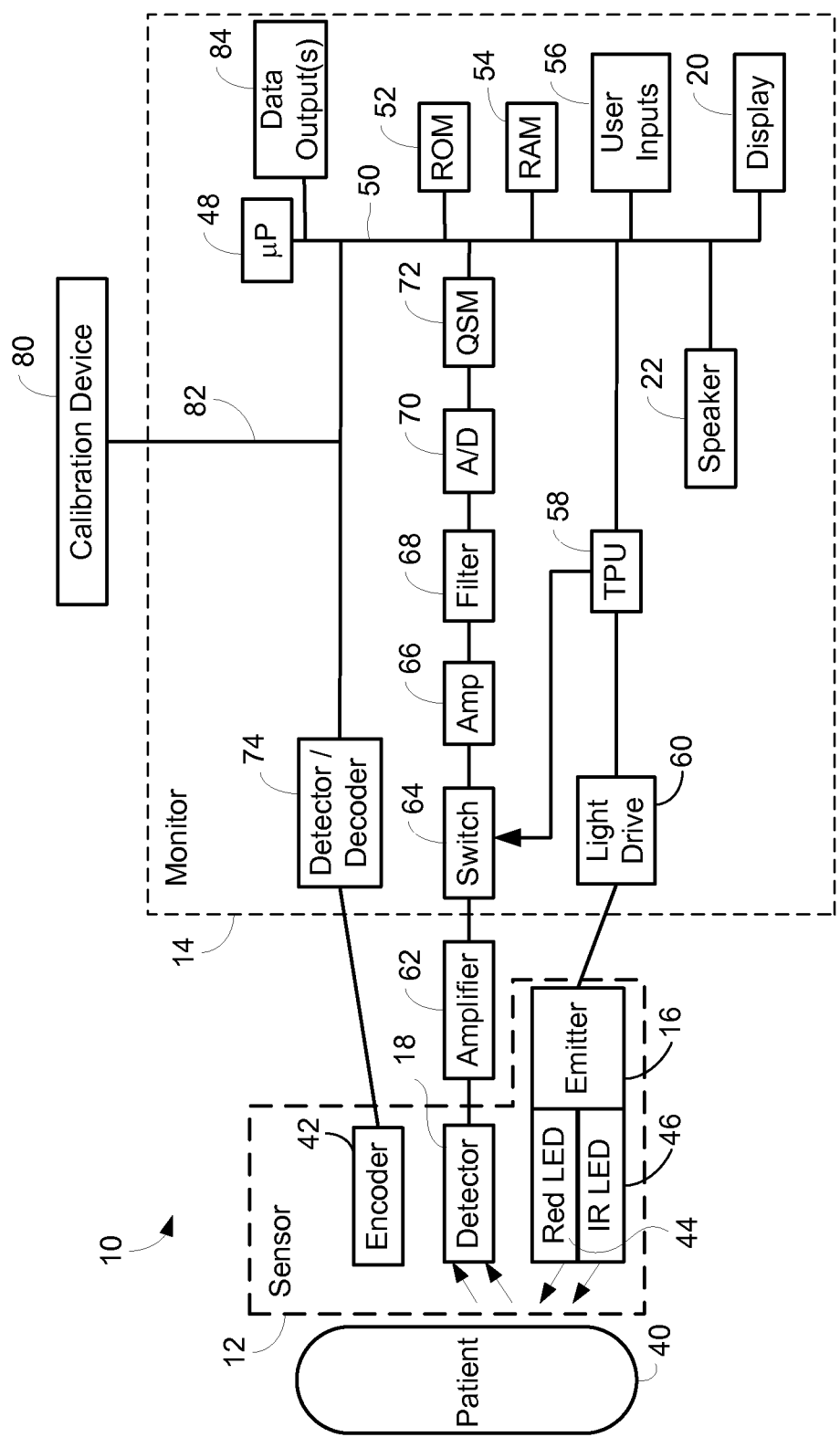
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42. Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics. In some embodiments, encoder 42 may include a memory on which one or more of the following information may be stored for communication to monitor 14; the type of the sensor unit 12; the wavelengths of light emitted by emitter 16; the particular wavelength each sensor in the sensor array is monitoring; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. Microprocessor 48 may also determine other information relating to the system 10, the physiological parameters or signals, or any other suitable information. In an exemplary embodiment, such information may include an artifact flag, a valid sample flag, and flags relating to the status of sensor 12 (e.g., whether sensor 12 is attached to monitor 14, whether sensor 12 is attached to patient 40, or whether sensor 12 is of an appropriate type for determining a physiological parameter such as respiration rate).

Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor 48 to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data output 84 may provide for communications with other devices such as display monitor 26 utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include PPG signals to be transmitted to display monitor module 26.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
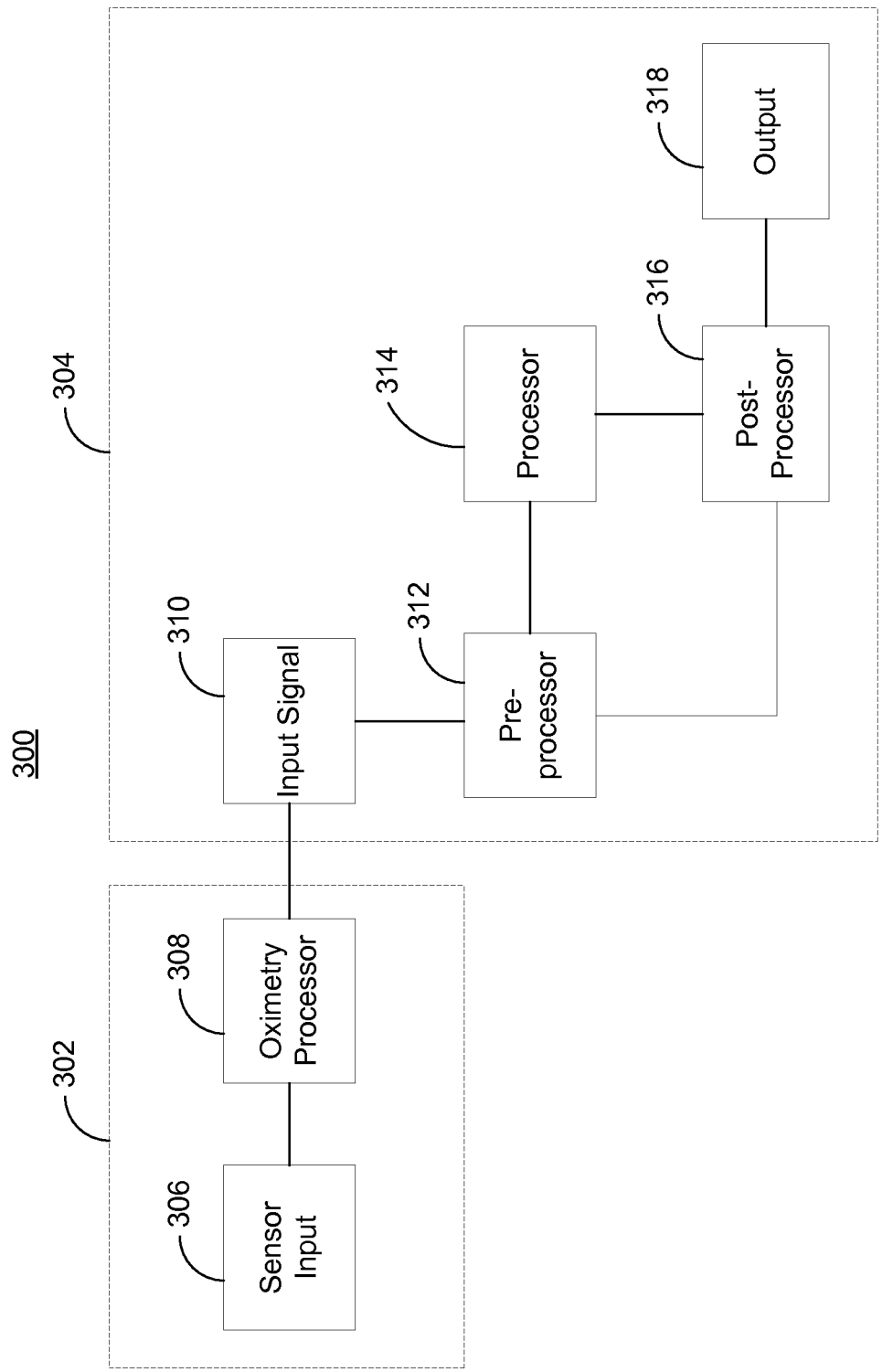
FIG. 3 shows a block diagram of an illustrative signal processing system in accordance with some embodiments of the present disclosure.

FIG. 3 is an illustrative processing system 300 in accordance with an embodiment that may implement the signal processing techniques described herein. In some embodiments, processing system 300 may be included in a patient monitoring system (e.g., patient monitoring system 10 of FIGS. 1-2). Processing system 300 may include monitor processing system 302 and display monitor processing system 304. Although in an exemplary embodiment monitor processing system 302 may be associated with monitor 14 and display monitor processing system 304 may be associated with display monitor 26, it will be understood that the components of monitor processing system 302 and display monitor processing system 304 may be located within any portion of system 10.

Monitor processing system 302 may include sensor input 306 and oximetry processor 308. In an exemplary embodiment sensor input 306 may correspond to the monitor 14 input from sensor 12 and oximetry processor 308 may correspond to the hardware of monitor 14 as depicted in FIG. 2. Oximetry processor 308 may generate a PPG signal, calculate values for physiological parameters, and generate a plurality of flags or status indicators based on the signal received from sensor input 306. Although it will be understood that the PPG signal may be generated in any suitable manner, in an exemplary embodiment values for the PPG signal may be sampled at 76 Hz and stored in memory of oximetry processor 308. Although it will be understood that oximetry processor 308 may calculate any suitable physiological parameters, in an exemplary embodiment the physiological parameters may include pulse rate and oxygen saturation ($SpO_2$) values. Although it will be understood that oximetry processor 308 may generate any suitable flags or indicators, in an exemplary embodiment oximetry processor may generate an artifact flag (e.g., indicating that an artifact has been detected), an invalid sample flag (e.g., indicating that a PPG sample is invalid), a sensor connection flag (e.g., indicating that the sensor is not connected to the monitor or is not properly connected to the monitor), or sensor status flag (e.g., indicating that the sensor is not a proper type for the monitor or for determining a physiological parameter of interest such as respiration).

The physiological values and flags may also be stored by oximetry processor 308, and may be associated with the PPG signal in a manner that allows the relative timing of all stored values and flags to be determined. The PPG signal, physiological values, and flags may be transmitted to display monitor processing system 304. Although the PPG signal, physiological values, and flags may be transmitted in any suitable manner, in an exemplary embodiment a sampling window (e.g., five seconds) of stored information may be transmitted to display monitoring system 304 on a periodic basis.

Display monitor processing system 304 may include input signal 310, pre-processor 312, processor 314, post-processor 316, and output 318. Pre-processor 312, processor 314, and post-processor 316 may be any suitable software, firmware, hardware, or combination thereof for calculating physiological parameters such as respiration information based on input signal 310. For example, pre-processor 312, processor 314, and post-processor 316 may include one or more hardware processors (e.g., integrated circuits), one or more software modules, computer-readable media such as memory, firmware, or any combination thereof. Pre-processor 312, processor 314, and post-processor 316 may, for example, be a computer or may be one or more chips (i.e., integrated circuits). Pre-processor 312, processor 314, and post-processor 316 may, for example, include an assembly of analog electronic components.

In the illustrated embodiment, input signal 310 include one or more of a PPG signal, physiological values (e.g., pulse rate or $SpO_2$), and related flags (e.g., artifact flag, invalid sample flag, and sensor status flags). The PPG signal may be sampled and generated at monitor 14, for example at 76 Hz. Input signal 310 may be coupled to pre-processor 312. In some embodiments, input signal 310 may include PPG signals corresponding to one or more light frequencies, such as a Red PPG signal and an IR PPG signal. In some embodiments, the signal may include signals measured at one or more sites on a patient's body, for example, a patient's finger, toe, ear, arm, or any other body site. In some embodiments, signal 310 may include multiple types of signals (e.g., one or more of an ECG signal, an EEG signal, an acoustic signal, an optical signal, a signal representing a blood pressure, and a signal representing a heart rate). The signal may be any suitable biosignal or signals, such as, for example, electrocardiogram, electroencephalogram, electrogastrogram, electromyogram, heart rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, and/or any combination thereof.

Pre-processor 312 may be implemented by any suitable combination of hardware and software. In an embodiment, pre-processor 312 may be any suitable signal processing device and the signal received from input signal 310 may include one or more PPG signals. An exemplary received PPG signal may be received in a streaming fashion, or may be received on a periodic basis as a sampling window (e.g., every 5 seconds). The received signal may include the PPG signal as well as other information related to the PPG signal (e.g., a pulse found indicator, pulse rate values, $SpO_2$ values, pulse rate values, the mean pulse rate from the PPG signal, the most recent pulse rate estimate, an indicator of invalid samples, an indicator of artifacts within the PPG signal, and information relating to the status of the sensor). It will be understood that input signal 310 may include any suitable signal source, signal generating data, signal generating equipment, or any combination thereof to be provided to pre-processor 312. The signal received at input signal 310 may be a single signal, or may be multiple signals transmitted over a single pathway or multiple pathways.

Pre-processor 312 may apply one or more signal processing operations to input signal 310. For example, pre-processor 312 may apply a pre-determined set of processing operations to input signal 310 to produce a signal that may be appropriately analyzed and interpreted by processor 314, post-processor 316, or both. Pre-processor 312 may perform any necessary operations to provide a signal that may be used as an input for processor 314 and post-processor 316 to determine physiological information such as respiration information. Examples include reshaping the signal for transmission, multiplexing the signal, modulating the signal onto carrier signals, compressing the signal, encoding the signal, filtering the signal, low-pass filtering, band-pass filtering, signal interpolation, downsampling of a signal, attenuating the signal, adaptive filtering, closed-loop filtering, any other suitable filtering, and/or any combination thereof. One example output of operations performed by pre-processor 312 may be to define a set of fiducial points that may be used a baseline to analyze the PPG signal (e.g., to determine respiration information).

Another example of operations performed by pre-processor 312 may be to identify one or more portions of an analysis window of data (e.g., a 45-second window of the 9 previous 5-second sampling windows) that may include invalid or questionable data. Although such portions of the data may be identified in any suitable manner, in an exemplary embodiment the portions of data may be identified based on one or more flags, PPG data, pulse rate values, or $SpO_2$ values as described herein. Pre-processor 312 may also modify the PPG signal based on the identified portions invalid or questionable data to generate a usable portion of the PPG signal. Although the PPG signal may be modified in any suitable manner, in an exemplary embodiment any samples of PPG data corresponding to invalid or questionable data may be removed from the analysis window of data, attenuated, or replaced with substitute data as described herein.

Other signal processing operations may be performed by pre-processor 312 for each pulse and may be related to producing morphology metrics suitable as inputs to determine physiological information. Pre-processor 312 may perform calculations based on an analysis window of a series of recently received PPG signal sampling windows (e.g., a 45-second analysis window may correspond to the 9 most recent 5-second sampling windows). The physiological information may be respiration information, which may include any information relating to respiration (e.g., respiration rate, change in respiration rate, breathing intensity, etc.). Because respiration has an impact on pulse characteristics, it may be possible to determine respiration information from a PPG signal. Morphology metrics may be parameters that may be calculated from the PPG signal that provide information related to respiration. Examples include a down metric for a pulse, kurtosis for a pulse, the delta of the second derivative between predetermined samples of consecutive pulses, the up metric for a pulse, skew, ratio of predetermined samples of a pulse or its first or second derivative (e.g., b/a ratio or c/a ratio), peak amplitude of a pulse, center of gravity of a pulse, or area of a pulse, as described in more detail herein. Other information that may be determined by pre-processor 312 may include the pulse rate, the variability of the period of the PPG signal, the variability of the amplitude of the PPG signal, and an age measurement indicative of the age of the usable portion of the analyzed PPG signal.

In some embodiments, pre-processor 312 may be coupled to processor 314 and post-processor 316. Processor 314 and post-processor 316 may be implemented by any suitable combination of hardware and software. Processor 314 may receive physiological information and calculated parameters from pre-processor 312. For example, processor 314 may receive morphology metrics for use in calculating morphology metric signals that may be used to determine respiration information, as well as pulse rate and an age for the morphology metric signals. For example, processor 314 may receive samples representing a number of morphology metric values, such as down metric calculations, kurtosis metric calculations, delta of the second derivative (DSD) metric calculations, and b/a ratio calculations from pre-processor 312. The down metric is the difference between a first (e.g., fiducial) sample of a fiducial-defined portion of the PPG signal and a minimum sample of the fiducial-defined portion of the PPG signal. The DSD metric is the delta (difference) between fiducial points in consecutive fiducial-defined portions of the second derivative of the PPG signal.

Figure 4:
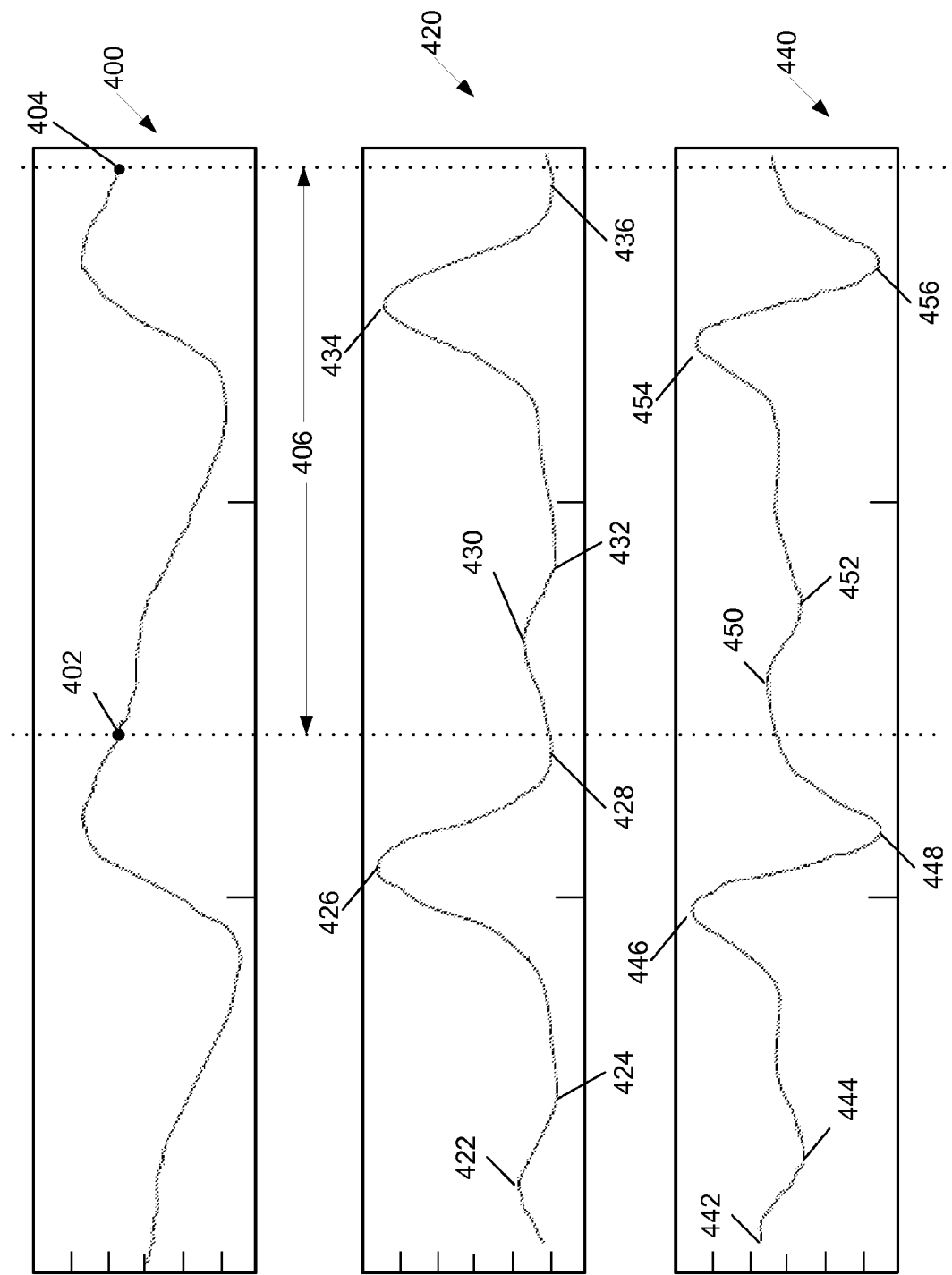
FIG. 4 shows an illustrative PPG signal, a first derivative of the PPG signal, and a second derivative of the PPG signal in accordance with some embodiments of the present disclosure.

The b/a ratio metric (i.e., b/a) is depicted in FIG. 4. FIG. 4 depicts an exemplary PPG signal 400, first derivative of the PPG signal 420, and second derivative of the PPG signal 440. The b/a ratio is based on the ratio between the a-peak and b-peak of the PPG signal 400, first derivative signal 420, or second derivative signal 440. In FIG. 4, the b/a ratio is depicted for the first derivative signal 420 and second derivative signal 440. Fiducial points 402 and 404 of PPG signal 400 define a fiducial-defined portion 406. Each of PPG signal 400, first derivate signal 420, and second derivative signal 440 may include a number of peaks (e.g., four peaks corresponding to maxima and minima) which may be described as the a-peak, b-peak, c-peak, and d-peak, with the a-peak and c-peak generally corresponding to local maxima within a fiducial-defined portion and the b-peak and d-peak generally corresponding to local minima within a fiducial-defined portion. For example, for first derivative signal 420 the a-peaks are indicated by points 426 and 434, the b-peaks by points 428 and 436, the c-peaks by points 422 and 430, and the d-peaks by points 424 and 432. The b/a ratio measures the ratio of the b-peak (e.g., 428 or 436) and the a-peak (e.g., 426 or 434). For second derivative signal 440 the a-peaks are indicated by points 446 and 454, the b-peaks by points 448 and 456, the c-peaks by points 442 and 450, and the d-peaks by points 444 and 452. The b/a ratio measures the ratio of the b-peak (e.g., 448 or 456) and the a-peak (e.g., 446 or 454).

Kurtosis measures the peakedness of a signal, such as the PPG signal, the first derivative of the PPG signal, or the second derivative of the PPG signal. In an exemplary embodiment, the kurtosis metric may be based on the first derivative of the PPG signal. The kurtosis of a signal may be calculated based on the following formulae:

$$D = \frac{1}{n}\sum_{i=1}^{n}(x'_i - \bar{x}')^2 \tag{14}$$

$$\text{Kurtosis} = \frac{1}{nD^2}\sum_{i=1}^{n}(x'_i - \bar{x}')^4 \tag{15}$$

where:
$x_i'$=ith sample of $1^{st}$ derivative;
$\bar{x}'$=mean of 1st derivative of fiducial-defined portion;
n=set of all samples in the fiducial-defined portion.

Processor 314 may utilize the received morphology metric values to calculate morphology metric signals and then to calculate respiration information signals and values from the morphology metric signals. Processor 314 may be coupled to post-processor 316 and may communicate respiration information to post-processor 316. Processor 314 may also provide other information to post-processor 316 such as the signal age related to the signal used to calculate the respiration information, a time ratio representative of the usable portion of the respiration information signal, or a confidence metric indicative of the strength of the respiration information signals. Pre-processor 312 may also provide information to post-processor 316 such as period variability, amplitude variability, and pulse rate information. Post-processor 316 may utilize the received information to calculate an output respiration information, as well as other information such as the age of the respiration information and status information relating to the respiration information output (e.g., whether a valid output respiration information value is currently available). Post-processor 316 may provide the output information to output 318.

Output 318 may be any suitable output device such as one or more medical devices (e.g., a medical monitor that displays various physiological parameters, a medical alarm, or any other suitable medical device that either displays physiological parameters or uses the output of post-processor 316 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In some embodiments, all or some of pre-processor 312, processor 314, and/or post-processor 316 may be referred to collectively as processing equipment. For example, processing equipment may be configured to amplify, filter, sample and digitize an input signal 310 and calculate physiological information from the signal.

Pre-processor 312, processor 314, and post-processor 316 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by pre-processor 312, processor 314, and post-processor 316 to, for example, store data relating to input PPG signals, morphology metrics, respiration information, or other information corresponding to physiological monitoring.

It will be understood that system 300 may be incorporated into system 10 (FIGS. 1 and 2) in which, for example, input signal 310 may be generated by sensor unit 12 (FIGS. 1 and 2) and monitor 14 (FIGS. 1 and 2). Pre-processor 312, processor 314, and post-processor 316 may each be located in one of monitor 14 or display monitor 26 (or other devices), and may be split among multiple devices such as monitor 14 or display monitor 26. In some embodiments, portions of system 300 may be configured to be portable. For example, all or part of system 300 may be embedded in a small, compact object carried with or attached to the patient (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In some embodiments, a wireless transceiver (not shown) may also be included in system 300 to enable wireless communication with other components of system 10. For example, communications between one or more of pre-processor 312, processor 314, and post-processor 316 may be over BLUETOOTH, 802.11, WiFi, WiMax, cable, satellite, Infrared, or any other suitable transmission scheme. In some embodiments, a wireless transmission scheme may be used between any communicating components of system 300.

Figure 5:
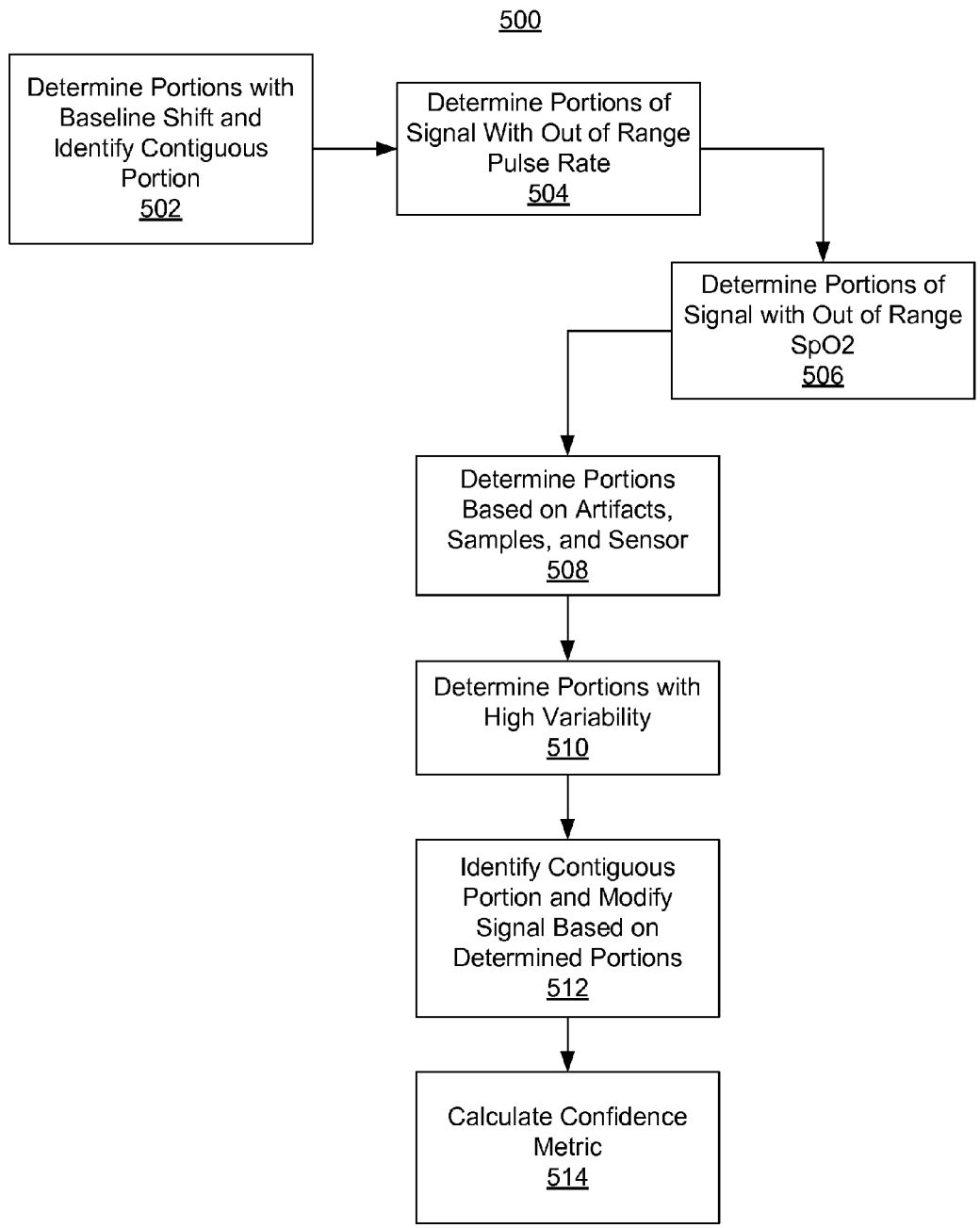
FIG. 5 is a flow diagram showing illustrative steps for identifying usable portions of a physiological signal in accordance with some embodiments of the present disclosure.

FIG. 5 depicts a flow diagram showing illustrative steps for determining a usable portion of a physiological signal such as a PPG signal in accordance with some embodiments of the present disclosure. Although a number of exemplary steps are disclosed herein, it will be understood that any of the steps depicted in FIG. 5 may be omitted, the order of the steps may be modified, and additional steps may be added. For example, any of the steps for determining signal portions (i.e., steps 502, 504, 506, 508, and 510) may be omitted, and additional signal portion identifying steps may be added. The steps including identifying contiguous signal portions may be performed as depicted in FIG. 5 (i.e., steps 502 and 512), after all signal portions are identified (e.g., at step 512 only), or may be performed individually after each signal portion is identified. Similarly, modifying the determined signal portions may be performed as depicted in FIG. 5 (i.e., at step 512), after some of the signal portions are identified (e.g., at steps 502 and 512), or may be performed individually after each signal portion is identified. In some embodiments different signal modification procedures may be associated with different signal portion determination steps.

At step 502, pre-processor 312 may identify any portions of the PPG signal having a large baseline shift and identify a contiguous portion of the PPG signal based on the identified portions. In an exemplary embodiment, step 502 may be performed prior to the other steps for determining portions of the PPG signal, such that only the contiguous portion of the PPG signal may be passed to steps 504-514. In other embodiments a set of indices or flags may be associated with the contiguous portion of the PPG signal identified in step 502, and the PPG signal may be passed to steps 504-514.

Figure 6:
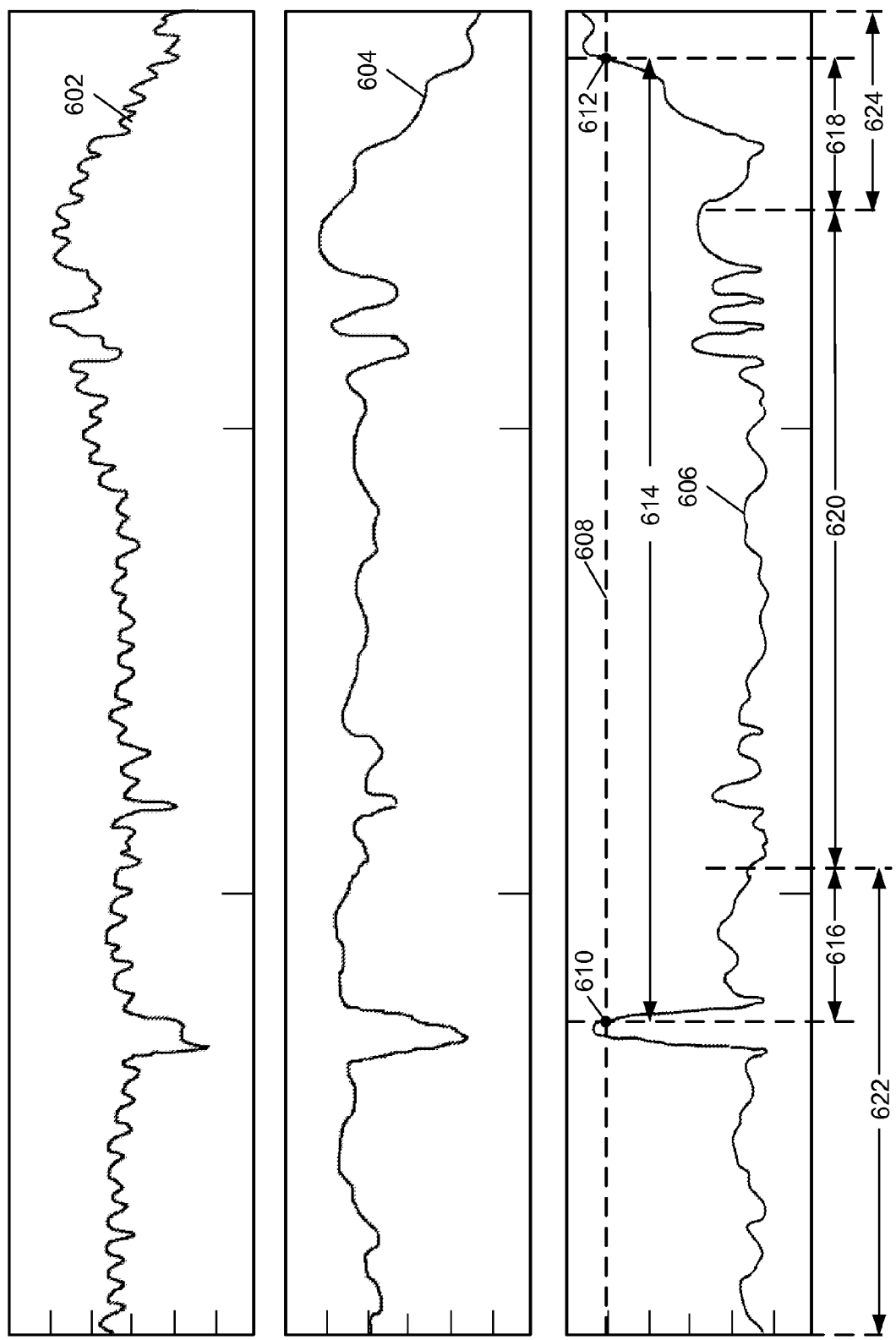
FIG. 6 shows an illustrative physiological signal, baseline signal, and absolute value of baseline signal in accordance with some embodiments of the present disclosure.

FIG. 6 shows an illustrative PPG signal 602, baseline signal 604, and absolute value signal 606 in accordance with some embodiments of the present disclosure. These exemplary signals may illustrate identifying a large baseline shift in accordance with some embodiments of the present disclosure. PPG signal 602 may be filtered to generate baseline signal 604. Although PPG signal 602 may be filtered in any suitable manner, in an exemplary embodiment PPG signal may be filtered with a 0.07 to 0.7 Hz $3^{rd}$ order Butterworth filter. To achieve zero phase change, PPG signal 602 may be filtered twice, once in each direction. A threshold 608 may be calculated from the baseline signal. The thresholds may be predetermined or may be dynamic and may be based on, for example, a moving average (weighted or fixed). In an exemplary embodiment threshold 808 may be based on the standard deviation of baseline signal 604 (e.g., a 2.9 times the standard deviation of baseline signal 604).

Absolute value signal 606 may be the generated based on the absolute value of baseline signal 604, and compared to threshold 608. Any locations where absolute value signal 606 crosses threshold 608 may be identified (e.g., crossing points 610 and 612). A longest contiguous signal portion 614 between crossing points may be identified. In some embodiments, longest contiguous signal portion 614 may be selected as the usable portion of PPG signal 602. In another embodiment, buffer regions 616 and 618 may be established from crossing points 610 and 612. Buffer regions 616 and 618 may ensure that the sections of data identified as the usable portion of PPG signal 602 are sufficiently far enough away from the portions of the signal that exhibit a large baseline shift. If buffer regions 616 and 618 are implemented, the excluded portions of PPG signal 602 may be the portions associated with signal portions 622 and 624, while the longest contiguous portion of PPG signal 602 may be signal portion 620. In an exemplary embodiment the portions of PPG signal 602 associated with signal portions 622 and 624 may be discarded. In other embodiments the portions of PPG signal 602 associated with signal portions 622 and 624 may be modified, set to zero, attenuated, replaced with white noise, or replaced with cyclical padding, as described herein.

Referring again to FIG. 5, at step 504, pre-processor 312 may identify portions of the PPG signal that have an out of range pulse rate. A series of pulse rate values may be associated with an analysis window of PPG data and may be determined in any suitable manner. In exemplary embodiments, the pulse rate values may be real-time pulse rate values (e.g., associated with a single pulse), an average of two or more pulse rate values (such as the last five pulse rates), or any other suitable pulse rate values. An average pulse rate value may be a weighted average based on, for example, signal quality, signal strength, or both. Each pulse rate value may be calculated using any suitable signal source for calculating pulse rate. For example, an ECG system may be used to generate the pulse rate. Alternatively, or in addition, the pulse oximeter may calculate the pulse rate from the PPG signal using any suitable processing technique. Each of the pulse rate values may be compared to one or more pulse rate thresholds. Although the pulse rate values may be compared to any suitable pulse rate thresholds, in an exemplary embodiment each pulse rate value may be compared to both a maximum pulse rate threshold and a minimum pulse rate threshold. The thresholds may be predetermined or may be dynamic and may be based on, for example, a moving average (weighted or fixed). Any samples of the PPG signal that are associated with an out of range pulse rate may be identified for further processing. For example, any PPG samples associated with pulse rate values falling outside of the pulse rate range established by the thresholds may be identified with indices or flags such that the associated portion of the PPG signal may be modified, discarded, down-weighted, or otherwise ignored as described herein.

At step 506, pre-processor 312 may identify portions of the PPG signal that have an out of range $SpO_2$ value. A series of $SpO_2$ values may be associated with an analysis window of PPG data and may be determined in any suitable manner. In exemplary embodiments, the $SpO_2$ values may be real-time $SpO_2$ values (e.g., associated with a single portion of the PPG signal), an average of two or more $SpO_2$ values (such as the last five $SpO_2$ values), or any other suitable $SpO_2$ values. An average $SpO_2$ value may be a weighted average based on, for example, signal quality, signal strength, or both. Each of the $SpO_2$ values may be compared to one or more $SpO_2$ thresholds. Although the $SpO_2$ values may be compared to any suitable $SpO_2$ thresholds, in an exemplary embodiment each $SpO_2$ value may be compared to both a maximum $SpO_2$ threshold and a minimum $SpO_2$ threshold. The thresholds may be predetermined or may be dynamic and may be based on, for example, a moving average (weighted or fixed). Any samples of the PPG signal that are associated with an out of range $SpO_2$ value may be identified for further processing. For example, any PPG samples associated with $SpO_2$ values falling outside of the $SpO_2$ range established by the thresholds may be identified with indices or flags such that the associated portion of the PPG signal may be modified, discarded, down-weighted, or otherwise ignored as described herein.

At step 508, pre-processor 312 may identify portions of the PPG signal that are likely to have data corruption due to one or more sources. A portion of the PPG signal may include data corruption for multiple reasons, such as motion artifacts, damaged or malfunctioning sensors, user error (e.g., improper sensor attachment or patient movement), improper connection of the sensor to a patient, etc. The system of the present disclosure may identify such data corruption in any suitable manner, including based on directly identifying the source of the data corruption (e.g., an unattached sensor) or based on characteristics of the PPG signal. For example, an artifact may present itself as a particular characteristic of the PPG signal, a metric calculated from the PPG signal, a particular morphology of the PPG signal, or any combination thereof that distorts the PPG signal or otherwise renders it not useable or of questionable use in deriving desired physiological information, such as respiration information. Artifacts may be caused by any of a variety of sources, such as patient motion, noise, connectivity problems, any other source, or any combination thereof. Invalid samples may be identified when the oximetry system is performing a hardware calibration, performing diagnostic self test, changing LED drive power, changing system gains, when the collected data is out of range for converter 70, or during the resetting of the signal conditioning components (e.g., amplifiers 64 and 68) of monitor 14. An improperly attached sensor may be identified based on any improper connection of the sensor 12 to the monitor 12 or patient 40. An invalid sensor may be identified based on an identification that the sensor 12 is of a sensor type (e.g., based on information stored in encoder 42) that is not appropriate for a particular application such as determining respiration information.

Although data corruption may be identified in any suitable manner, in an exemplary embodiment the system of the present disclosure may generate flags or indices that correspond to the occurrence of particular conditions that may cause data to become corrupted. Although any suitable flags may be used to identify portions of the PPG signal, in an exemplary embodiment the flags may include an artifact flag, an invalid sample flag, a sensor connection flag, a sensor off patient flag, and an invalid sensor flag. As is described herein, each of the flags may be associated with the PPG signal such that the samples of the PPG signal corresponding to the flags may be identified.

Any samples of the PPG signal that are associated with one of these corrupted data may be identified so that they may be appropriately dealt with in further processing. For example, any PPG samples associated with a corrupted data portion may be identified such that the associated portion of the PPG signal may be modified, discarded, down-weighted or otherwise ignored as described herein.

At step 510, pre-processor 312 may analyze the PPG signal to determine whether any portions of the PPG signal exhibit a high pulse-to-pulse variability. Although in an exemplary embodiment the pulse-to-pulse variability may be determined, it will be understood that any suitable measure of signal variability may be utilized in accordance with the present disclosure. For example, any statistical analysis may be used to determine variability, such as standard deviation, statistical variability (e.g., of the standard deviation), difference in mean, difference in median, or any suitable combination thereof. Any suitable pulse characteristics may be used as the basis for the variability calculation, including pulse period, pulse amplitude, pulse skew, pulse slope, location of pulse features (e.g., signal notches, etc.), or any combination thereof.

Although the portions of the PPG signal having a high pulse-to-pulse variability may be identified in any suitable manner, in an exemplary embodiment pre-processor 312 may compare the periods of each consecutive set of pulses of PPG data. This difference may then be divided by a pulse period value associated with some or all of an analysis window of PPG data. The pulse period value may be determined in any suitable manner, such as based on a mean, median, or average of some or all of the analysis window of PPG data. In an exemplary embodiment the pulse period value may be a mean pulse period value for the analysis window. Although the mean pulse period value may be determined in any suitable manner, in an exemplary embodiment the mean pulse period value may be based on a mean pulse rate for the analysis window. If the pulse-to-pulse period variation value exceeds a threshold, any samples of the PPG signal that are associated with the consecutive pulses may be identified for further processing. The threshold may be predetermined or may be dynamic and may be based on, for example, a moving average (weighted or fixed). Any PPG samples associated with the consecutive pulses may be identified with a flag or indices such that the associated portion of the PPG signal may be modified, discarded, down-weighted or otherwise ignored as described herein.

Figure 7:
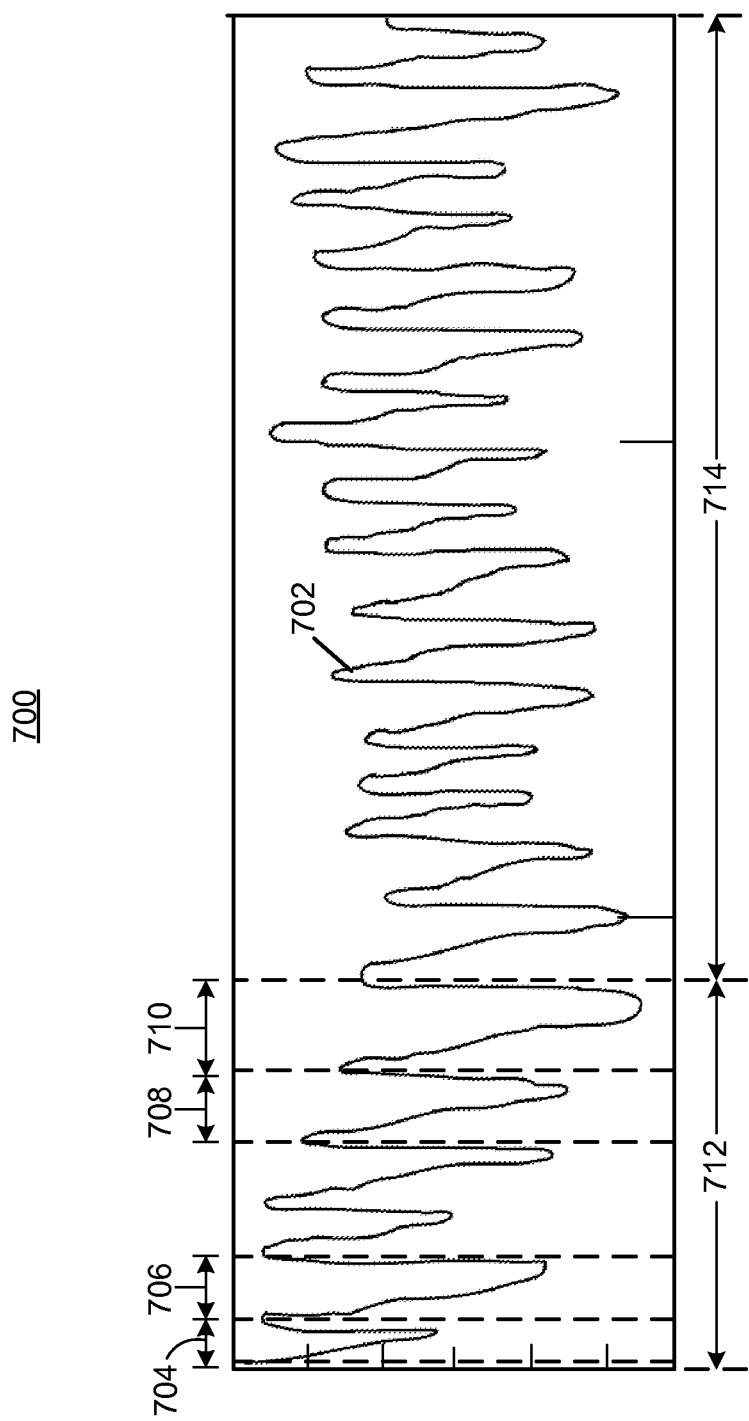
FIG. 7 shows an illustrative physiological signal having portions with a large pulse-to-pulse variability in accordance with some embodiments of the present disclosure.

An example of PPG signal 702 having a large pulse-to-pulse variability is depicted in FIG. 7. Consecutive sets of pulses having a large pulse-to-pulse variability may include pulses 704 and 706 and pulses 708 and 710. In an exemplary embodiment, the mean pulse period for PPG signal 702 may be 0.75 seconds (i.e., based on pulse rate of 80 beats per minute). A pulse period for pulse 704 may be 0.6 seconds, while a pulse period for pulse 706 may be 1.0 seconds. Based on these exemplary values, the pulse-to-pulse variability may be 40% (i.e., (0.9 s−0.6 s)/0.75 s). If an exemplary threshold is 30%, any samples of PPG signal 702 that are associated with pulses 704 or 706 may be identified for further processing. Similarly, a pulse period for pulse 708 may be 1.0 seconds, while a pulse period for pulse 710 may be 1.5 seconds. Based on these exemplary values, the pulse-to-pulse variability may be 67% (i.e., (1.5 s−1.0 s)/0.75 s). If an exemplary threshold is 30%, any samples of PPG signal 702 that are associated with pulses 708 or 710 may be determined to have a high pulse-to-pulse variability. A contiguous section 714 of PPG signal 702 may be identified, and the section 712 associated with pulses 708 or 710 may be identified with indices or flags such that the associated portion of the PPG signal may be modified, discarded, down-weighted, or otherwise ignored as described herein.

Referring again to FIG. 5, processing may continue to step 512. At step 512, pre-processor 312 may identify a contiguous portion of the PPG signal that does not include the portions determined in steps 504-510 (e.g., if a contiguous portion determined in step 502 was already identified and processed in step 502), and modify, discard, down-weight or otherwise ignore the determined portions from steps 504-510. Although in an exemplary embodiment the contiguous portion of the PPG signal may be identified and the determined portions may be modified, discarded, down-weighted or otherwise ignored after all of steps 504-510 are completed, it will be understood that these operations may be performed after each of steps 504-510, or after some subset of steps 504-510, with subsequent processing performed on the PPG signal. It will also be understood that the processing associated with step 502 could also be performed at step 512.

Figure 8:
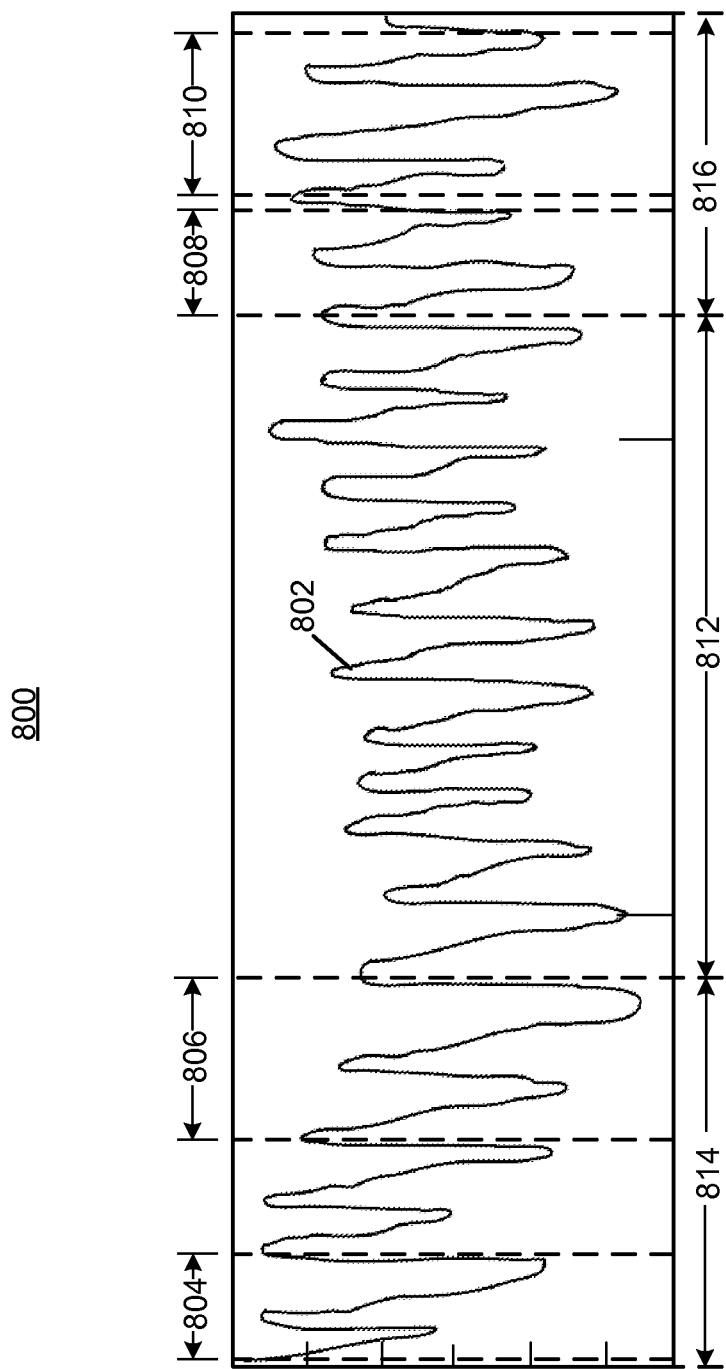
FIG. 8 shows an illustrative physiological signal having portions identified as including invalid or questionable data in accordance with some embodiments of the present disclosure.

FIG. 8 depicts an exemplary PPG signal 802 having a plurality of portions identified as including invalid or questionable data as determined by one or more of steps 502-508. In an exemplary embodiment PPG signal portions 804 and 806 may be identified has having a high pulse-to-pulse variability, PPG signal portion 808 may be identified as having an artifact, and PPG signal portion 810 may be identified as having out of range $SpO_2$ values. In an exemplary embodiment the largest contiguous portion of PPG signal 802 that does not include invalid or questionable data may be identified. For the exemplary signal depicted in FIG. 8 this may be PPG signal portion 812. In one embodiment, only PPG signal portion 812 may be retained as the usable portion of PPG signal 802. In another embodiment, other PPG signal portions corresponding to signal portions 804, 806, 808, and 810 may be modified to retain a complete analysis window of data. For example, signal portions 814 and 816 may correspond to signal portions 804, 806, 808, and 810 and one or more adjacent signal portions. One exemplary modification may be to replace each of signal portions 814 and 816 with an attenuated or zero magnitude signal. Another exemplary modification may be to replace each of signal portions 814 and 816 with white noise. Another exemplary modification may be to replace each of signal portions 814 and 816 with cyclical padding (i.e., replacing the invalid or questionable portions of PPG signal 802 with copies of adjacent usable portions of PPG signal 802).

In another exemplary embodiment the signal portions 814 and 816 may be identified for future processing, for example, with indices identifying signal portions 814 and 816. The indices may be utilized in any additional signal processing operations of PPG signal 802, for example, to down-weight PPG signal 802. Although down-weighting may be applied to any suitable signal processing operation, in an exemplary embodiment PPG signal 802 may be down-weighted for determining a value of a physiological parameter (e.g., by providing additional weight to one or more previously calculated values). Down-weighting may be implemented in any suitable manner, such as down-weighting only signal portions 814 and 816, or down-weighting the entire signal 802 based on the relative proportion of the usable signal (e.g., the percentage of usable signal 812 vs. the percentage of signal portions 814 and 816).

Referring again to FIG. 5, processing may continue to step 514. At step 514, pre-processor 312 may calculate a confidence metric for use in determining physiological information from the modified PPG signal. Although a confidence metric may be determined in any suitable manner, in an exemplary embodiment the confidence metric may be based on the percentage of the PPG signal that was determined to be usable by pre-processor 312, the reason that portions of the PPG signal were determined to unusable, or both. Although the confidence metric may be used for any suitable purpose in determining physiological information, in an exemplary embodiment the processor 314 or post-processor 316 may provide more averaging with prior physiological values when the confidence metric has a low value.

Figure 9:
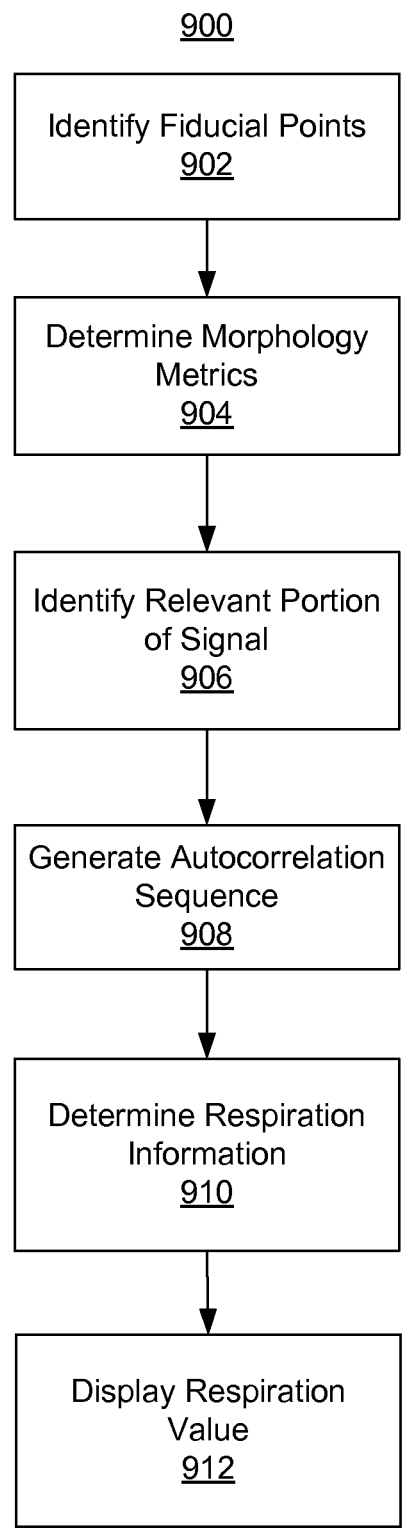
FIG. 9 is a flow diagram showing illustrative steps for determining respiration information from a photoplethysmograph signal in accordance with some embodiments of the present disclosure.

FIG. 9 depicts a flow diagram showing illustrative steps for determining physiological information such as respiration information from a physiological signal such as a PPG signal in accordance with some embodiments of the present disclosure. Although an exemplary embodiment is described herein, it will be understood that each of steps 900 may be performed by pre-processor 312, processor 314, post-processor 316, or any combination thereof. It will also be understood that steps 900 may be performed in alternative sequence or in parallel, that steps may be omitted, and that additional steps may be added or inserted.

At step 902 pre-processor 312 may identify fiducial points for successive pulse waves of a PPG signal. Fiducial points may be identified in any suitable manner, for example based on peaks, troughs, slope values (e.g., the maximum slope of the PPG signal), and/or predetermined offsets. An example of determining fiducial points for a PPG signal is described in more detail in co-pending, commonly assigned U.S. patent application Ser. No. 13/243,907, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. The fiducial points may define a series of fiducial defined portions that may be used as a reference for subsequent calculations, e.g., of morphology metric signals.

At step 904 pre-processor 312 may generate morphology metrics from the PPG signal. Morphology metrics may be calculated from the PPG signal in any suitable manner. In one embodiment, a plurality of morphology metrics may be generated from the PPG signal. Example morphology metrics that may be relevant to determining a physiological parameter such as respiration information from a PPG signal may include a down metric, a kurtosis metric, a delta of second derivative (DSD) metric, an up metric, a skew metric, a ratio of samples metric (e.g., a b/a ratio metric or c/a ratio metric), a i_b metric, a peak amplitude metric, a center of gravity metric, and an area metric. In an exemplary embodiment, morphology metric signals may be generated for the down metric, kurtosis metric, DSD metric, and b/a ratio metric. For each morphology metric a set of morphology metric values, each corresponding to a fiducial defined portion, may be calculated. The sets of morphology metric values may be communicated to processor 314 to be attenuated, interpolated, and filtered to generate the morphology metric signals. Generating morphology metric signals from a PPG signal is described in more detail in co-pending, commonly assigned U.S. patent application Ser. No. 13/243,853, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety.

At step 906, pre-processor 312 may determine a usable portion of the PPG signal as described herein. In an exemplary embodiment, only a usable portion of the PPG signal may be passed to processor 314. Pre-processor 312 may also determine a confidence metric for the usable portion of the PPG signal as described herein.

At step 908, processor 314 may generate an autocorrelation sequence from the morphology metric signal. Although an autocorrelation sequence may be generated in any suitable manner, in one embodiment an autocorrelation sequence may be generated for each morphology metric signal and the autocorrelation sequences may be combined into a single autocorrelation sequence based on weighting factors. Generating the autocorrelation sequence from the morphology metric signals is described in more detail in co-pending, commonly assigned U.S. patent application Ser. No. 13/243,951, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety.

At step 910, processor 314 may determine respiration information based on the autocorrelation sequence. Respiration information may be determined from the autocorrelation sequence in any suitable manner. In one exemplary embodiment, a continuous wavelet transform may be used to determine respiration information such as respiration rate from the autocorrelation sequence, as is described in more detail in co-pending, commonly assigned U.S. patent application Ser. No. 13/243,892, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. In another exemplary embodiment, respiration information may be determined directly from the autocorrelation sequence, (e.g., by comparing the peaks of the autocorrelation sequence to a threshold value or by identifying a maximum peak of the autocorrelation sequence within a window of interest). Determining respiration information directly from the autocorrelation sequence is described in more detail in co-pending, commonly assigned U.S. patent application Ser. No. 13/243,785, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. As is described in more detail herein, the determination of respiration information may be modified based on a historical distribution of respiration values. The output respiration value may be communicated to post-processor 316.

At step 912, post-processor 316 may determine a display respiration value to be displayed (e.g., at the patient monitoring system). The display respiration value may be determined in any suitable manner. For example, the display respiration value may be based on the currently received respiration value. In another exemplary embodiment, the display respiration value may be based on the received respiration value as well as previously received respiration values. In an exemplary embodiment, post-processor 316 may calculate the display respiration value from the respiration value for the current analysis window and respiration values for one or more previous analysis windows, (e.g., the five previous analysis windows). In an exemplary embodiment, the relative weighting for the current respiration value for the current analysis window and respiration values for one or more previous analysis windows may be based on a confidence value.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for determining physiological information from a PPG signal, the method comprising:
receiving at an input of a pulse oximeter monitor the PPG signal generated by a pulse oximetry sensor;
determining, using a pulse oximeter monitor, a presence of an artifact in a first portion of the PPG signal;
determining, using the pulse oximeter monitor, a presence of a baseline shift that exceeds a baseline shift threshold in a second portion of the PPG signal;
determining, using the pulse oximeter monitor, a pulse-to-pulse variability that exceeds a variability threshold in a third portion of the PPG signal; and
identifying, using the pulse oximeter monitor, a contiguous portion of the PPG signal that does not include the first portion, the second portion, and the third portion, wherein the contiguous portion is at least a minimum length;
determining, using the pulse oximeter monitor, the physiological information based on the contiguous portion; and
indicating on the pulse oximeter monitor the physiological information.

2. The method of claim 1, further comprising discarding portions of the PPG signal that correspond to the first portion, the second portion, and the third portion.

3. The method of claim 1, further comprising replacing portions of the PPG signal that correspond to the first portion, the second portion, and the third portion with a respective substitute signal.

4. The method of claim 3, wherein replacing portions of the PPG signal comprises substituting an attenuated signal for portions of the PPG signal that correspond to the first portion, the second portion, and the third portion.

5. The method of claim 3, wherein replacing portions of the PPG signal comprises substituting cyclical padding for portions of the PPG signal that correspond to the first portion, the second portion, and the third portion.

6. The method of claim 1, wherein determining the presence of a baseline shift comprises:
identifying one or more locations in the PPG signal wherein a PPG baseline signal exceeds the baseline shift threshold; and
identifying the second portion based on the one or more locations and based on a buffer region between the one or more locations.

7. The method of claim 1, wherein determining the pulse-to-pulse variability comprises:
determining a mean pulse period associated with the PPG signal; and
determining the pulse-to-pulse variability based on the mean pulse period.

8. A non-transitory computer-readable storage medium interfaced with a pulse oximeter monitor for use in determining physiological information from a PPG signal received from a pulse oximetry sensor, the non-transitory computer-readable medium having computer program instructions recorded thereon for:
determining a presence of an artifact in a first portion of the PPG signal;
determining a presence of a baseline shift that exceeds a baseline shift threshold in a second portion of the PPG signal;

determining a pulse-to-pulse variability that exceeds a variability threshold in a third portion of the PPG signal;

identifying a contiguous portion of the PPG signal that does not include the first portion, the second portion, and the third portion, wherein the contiguous portion is at least a minimum length; and determining the physiological information based on the contiguous portion; and indicating on the pulse oximeter monitor the physiological information.

9. The non-transitory computer-readable medium of claim 8, the non-transitory computer-readable medium having computer program instructions recorded thereon for discarding portions of the PPG signal that correspond to the first portion, the second portion, and the third portion.

10. The non-transitory computer-readable medium of claim 8, the non-transitory computer-readable medium having computer program instructions recorded thereon for replacing portions of the PPG signal that correspond to the first portion, the second portion, and the third portion with a respective substitute signal.

11. The non-transitory computer-readable medium of claim 10, wherein replacing portions of the PPG signal comprises substituting an attenuated signal for portions of the PPG signal that correspond to the first portion, the second portion, and the third portion.

12. The non-transitory computer-readable medium of claim 8, wherein determining the presence of a baseline shift comprises:
   identifying one or more locations in the PPG signal wherein a PPG baseline signal exceeds the baseline shift threshold; and
   identifying the second portion based on the one or more locations and based on a buffer region between the one or more locations.

13. The non-transitory computer-readable medium of claim 8, wherein determining the pulse-to-pulse variability comprises:
   determining a mean pulse period associated with the PPG signal; and
   determining the pulse-to-pulse variability based on the mean pulse period.

14. A patient monitoring system comprising processing circuitry a pulse oximeter monitor configured to:
   determine a presence of an artifact in a first portion of a PPG signal;
   determine a presence of a baseline shift that exceeds a baseline shift threshold in a second portion of the PPG signal;
   determine a pulse-to-pulse variability that exceeds a variability threshold in a third portion of the PPG signal; and
   identify a contiguous portion of the PPG signal that does not include the first portion, the second portion, and the third portion, wherein the contiguous portion is at least a minimum length;
   determine physiological information based on the contiguous portion; and
   indicate on the pulse oximeter monitor the physiological information.

15. The patient monitoring system of claim 14, wherein the pulse oximeter monitor is further configured to discard portions of the PPG signal that correspond to the first portion, the second portion, and the third portion.

16. The patient monitoring system of claim 14, wherein the pulse oximeter monitor is further configured to replace portions of the PPG signal that correspond to the first portion, the second portion, and the third portion with a respective substitute signal.

17. The patient monitoring system of claim 16, wherein the pulse oximeter monitor is further configured to substitute an attenuated signal for portions of the PPG signal that correspond to the first portion, the second portion, and the third portion.

18. The patient monitoring system of claim 16, wherein the processing circuitry is further configured to substitute cyclical padding for portions of the PPG signal that correspond to the first portion, the second portion, and the third portion.

19. The patient monitoring system of claim 14, wherein the processing circuitry is further configured to:
   identify one or more locations in the PPG signal wherein a PPG baseline signal exceeds the baseline shift threshold; and
   identify the second portion based on the one or more locations and based on a buffer region between the one or more locations.

20. The patient monitoring system of claim 14, wherein the processing circuitry is further configured to:
   determine a mean pulse period associated with the PPG signal; and
   determine the pulse-to-pulse variability based on the mean pulse period.

* * * * *